United States Patent [19]

Luderer et al.

[11] Patent Number: 4,917,801

[45] Date of Patent: Apr. 17, 1990

[54] LYMPHOCYTE COLLECTION TUBE

[75] Inventors: Albert A. Luderer, Marshfield, Mass.; Ward C. Smith, Corning, N.Y.

[73] Assignee: Becton Dickinson and Company, Franklin Lakes, N.J.

[21] Appl. No.: 117,396

[22] Filed: Nov. 2, 1987

Related U.S. Application Data

[63] Continuation of Ser. No. 864,443, May 16, 1986, abandoned, which is a continuation of Ser. No. 678,100, Dec. 4, 1984, abandoned, which is a continuation-in-part of Ser. No. 544,125, Oct. 21, 1983, abandoned.

[51] Int. Cl.$^4$ ............................................. B01D 21/26
[52] U.S. Cl. .................................... 210/516; 422/101
[58] Field of Search ................................. 494/16–20; 422/101; 210/359, 516, 518

[56] References Cited

U.S. PATENT DOCUMENTS

| | | | |
|---|---|---|---|
| 3,852,194 | 12/1974 | Zine, Jr. ................. | 210/789 |
| 3,920,549 | 11/1975 | Gigliello et al. ........ | 210/789 |
| 3,945,928 | 3/1976 | Ayres ..................... | 210/516 |
| 3,960,727 | 6/1976 | Hochstrasser ........... | 210/782 |
| 4,101,422 | 7/1978 | Lamont et al. .......... | 210/789 |
| 4,147,628 | 4/1979 | Bennett et al. ......... | 210/516 |
| 4,153,739 | 5/1979 | Kessler .................. | 427/2 |
| 4,190,535 | 2/1980 | Luderer et al. ......... | 210/789 |
| 4,255,256 | 3/1981 | Ferrante et al. ........ | 210/789 |
| 4,310,430 | 1/1982 | Ichikawa et al. ....... | 210/782 |
| 4,350,593 | 9/1982 | Kessler .................. | 210/516 |
| 4,417,981 | 11/1983 | Nugent ................... | 210/516 |
| 4,435,293 | 3/1984 | Graham, Jr. et al. .... | 210/782 |
| 4,436,631 | 3/1984 | Graham, Jr. et al. .... | 210/518 |
| 4,457,782 | 7/1984 | Honda et al. ........... | 210/516 |
| 4,487,700 | 12/1984 | Kanter ................... | 210/789 |
| 4,534,798 | 8/1985 | Honda et al. ........... | 210/510.1 |
| 4,640,785 | 2/1987 | Carroll et al. .......... | 210/782 |
| 4,707,276 | 11/1987 | Dodge et al. ........... | 210/516 |
| 4,751,001 | 6/1988 | Saunders ................ | 210/516 |
| 4,816,168 | 3/1989 | Carrol et al. ........... | 210/516 |

FOREIGN PATENT DOCUMENTS 1127537 7/1982 Canada .
0036168 9/1981 European Pat. Off. .

OTHER PUBLICATIONS

Rickwood, D.; Iodinated Density Gradient Media, IRL Press (1983), pp. 147–171.
Luderer et al., Rapid, Quantitative Human Lymphocyte Separation and Purification in a Closed System, Molecular Immunology, 16 (1979), 621–624.
Nicholson et al., Comparison of T and B Cell Analyses on Fresh and Aged Blood, pp. 29–40, 1984, J of Immunological Methods, 73.
Experimental Cell Research, Splinter et al.
9265 X, Chemical Abstract.

Primary Examiner—W. Gary Jones
Attorney, Agent, or Firm—Hoffmann & Baron

[57] ABSTRACT

This invention relates to an assembly for centrifugally separating lymphocytes and monocytes from the heavier phases in samples of human blood utilizing a liquid density gradient medium. The particular inventive subject matter concerns the use of novel partition means initially separating the liquid density gradient medium from the sample of blood and designs for such partition means.

17 Claims, 1 Drawing Sheet

LYMPHOCYTE COLLECTION TUBE

This a continuation of co-pending application Ser. No. 864,443 filed on May 16, 1986, now abandoned, which is a continuation of Ser. No. 678,100 filed Dec. 4, 1984, abandoned, which is a continuation-in-part of Ser. No. 544,125 filed Oct. 21, 1983, abandoned.

BACKGROUND OF THE INVENTION

Considerable research has been conducted in recent years to develop improved means for the separation and collection of lymphocytes from human blood. An impetus for such research has been generated by the need for histocompatibility determinations in patients requiring organ transplants. A measure of lymphocyte function is critical to adjudge the type and level of medication necessary for immunosuppression.

One well-known method for isolating and collecting lymphocytes from anticoagulated human blood drawn via conventional phlebotomy techniques utilizes buoyant density centrifugation of blood cells. A newtonian fluid, frequently Ficoll-Paque ®, a liquid density gradient medium having a specific gravity of about 1.077 g/cc marketed by Pharmacia Fine Chemicals AB, Uppsala, Sweden, constitutes the medium. The method commonly involves the four general steps:

(a) a predetermined quantity of the Ficoll-Paque ® medium is run into the bottom of a test tube;

(b) a sample of whole or diluted blood is carefully pipetted onto the medium;

(c) the test tube is placed in a centrifuge and the blood-medium combination centrifuged at about 400–500 G's for about 30–40 minutes to cause the components of the blood having specific gravities greater than the medium, viz. >1.077 g/cc, to pass through the liquid; and thereafter, (d) the lymphocytes, which have a specific gravity less than 1.077 g/cc, are pipetted off the medium.

Several problems or concerns have been found to be inherent in that technique. For example:

(1) if, during the pipetting of the blood sample into the separation medium, lymphocytes are inadvertently diffused below the surface of the medium, the specific gravity of the medium in that area is so reduced as to become inadequate to separate the lymphocytes;

(2) if, during centrifugation, lighter phases in the blood migrate into the separation medium, they cannot pass upward therethrough because the buoyant force generated by 400–500 G's is insufficient;

(3) centrifugation forces in excess of about 400–500 G's cannot be employed with Ficoll-Paque ® medium as it is somewhat water soluble and higher centrifugation forces increase this solubility, thereby leading to a change in its specific gravity; and (4) after centrifugation has been completed, the pipetting of the lymphocytes off the surface of the separation medium must be conducted with substantial care because of the newtonian character of the Ficoll-Paque ® medium.

Numerous suggestions have been proposed for improving upon that technique. Several disclosures of such suggestions are recorded below.

U.S. Pat. No. 3,852,194 describes a process for isolating lighter phases from heavier fractions in human blood utilizing a thixotropic, gel-like material having a specific gravity which is intermediate to that of the phases to be separated. Upon centrifuging the gel and blood sample together, the gel exhibits sufficient flow to form a barrier between the lighter and heavier phases. That barrier enables the phase resting thereupon to be easily withdrawn therefrom using conventional laboratory techniques.

The patent postulates the operability of numerous gel-like substances; those substances complying with three general criteria:

(1) a specific gravity intermediate to that of the phases to be separated;

(2) chemical inertness to the phases of human blood; and (3) essentially non-flowable when at rest (thixotropic).

U.S. Pat. No. 3,920,549 is asserted to comprise an improvement upon the disclosure of U.S. Pat. No. 3,852,194. That improvement involved the use of a solid element, termed an "energizer", having a specific gravity greater than that of the gel-like substance. This energizer, during centrifugation, impacts upon the gel, which is normally placed in the bottom of a blood collection tube, thereby expediting the upward movement of the gel along the walls of the tube. In this manner the energizer accelerates the isolation of the blood phases and permits a cleaner separation therebetween.

U.S. Pat. No. 4,190,535 is specifically drawn to a procedure for isolating lymphocytes, monocytes, and platelets from anticoagulated blood. The process contemplates three general steps:

(1) a water-insoluble, thixotropic gel-like substance having a specific gravity between about 1,065–1.077 g/cc and exhibiting chemical inertness to blood components is deposited into a sample of anticoagulated blood;

(2) the gel-blood combination is centrifuged at a force of at least 1200 G's for a sufficient length of time that the gel forms a barrier between the heavier blood cells and the lymphocytes, monocytes, and platelets; and then (3) lymphocytes, monocytes, and platelets are removed from atop the barrier.

The patent observes that, because a non-newtonian, water-insoluble gel-like material capable of forming a barrier at centrifugation forces of in excess of 1200 G's is used, a faster and more complete separation was possible than with Ficoll-Paque ® medium. The patent also observes that the elimination of the liquid density gradient medium avoids the time-consuming process of layering two liquids without mixing them.

U.S. application Ser. No. 528,401, filed Sept. 1, 1983 in the names of Richard J. Carroll, Albert A. Luderer, and Anthony R. Zine, Jr., and under the title of SEPARATION OF LYMPHOCYTES AND MONOCYTES FROM AGED BLOOD, is directed to improving the quality of the separation of lymphocytes and monocytes from aged samples of anticoagulated human blood by inhibiting the shift observed in the buoyant density of granulocyte white blood cells. The inventive process involves four general steps:

(1) a sample of anticoagulated blood is mixed with a hypertonic fluid containing an organic or inorganic ionic substance of relatively low molecular weight and which is chemically compatible with components of the blood;

(2) a water-insoluble thixotropic gel-like substance similar to that described in U.S. Pat. No. 4,190,535 with a specific gravity between 1.060–1.075 g/cc is deployed into the blood-hypertonic fluid mixture;

(3) the gel-blood-hypertonic fluid sample is centrifuged at a force of at least 1200 G's to cause the gel to form a barrier between the lymphocytes and monocytes and the heavier cells of the blood; and then (4) the lymphocytes and monocytes are withdrawn from atop that barrier.

Whereas each of the above-discussed disclosures does indeed modify and improve upon various aspects of the well-known Ficoll-Paque ® medium technique, none of them is able to equal or improve upon the performance of the liquid medium with respect to the purity of the separated cell population. Because purity is a critical parameter in cell separation, the above-discussed disclosures cannot be substituted for the Ficoll-Paque ® medium technique in all applications. Consequently, research has continued in an effort to formulate simpler methods of cell separation which utilize a liquid medium. More particularly, a process has been sought which eliminates the time-consuming procedure necessary to layer blood samples onto the liquid density gradient medium without encountering mixing at the interface between the two liquids. This layering process generally requires about three minutes/tube to flow the blood sample down the inside wall of the tube at a rate which will permit layering and avoid turbulence at the interface. Inasmuch as this procedure is conducted manually and two tubes are conventionally prepared per sample, the setup time for readying a group of ten tubes may require a period of greater than one hour. The time involved in the centrifuging step is less critical since many tubes can be processed at the same time. Further simplification of the setup procedure could be accomplished if the patient's blood sample could be drawn directly into the centrifuge tube, thereby removing the need for transferring the sample form the collection tube to the centrifuge tube. In many instances it is desirable to add a reagent to the blood sample prior to cell separation to anticoagulate the blood, dilute the blood, or modify physical and/or chemical characteristics of the blood components.

Therefore, a primary objective of the present invention is to provide a series of devices which, separately or in combination, will not only satisfy the range of needs of research workers and diagnostic technicians who may merely wish to eliminate the layering problem or to minimize setup time, but also will provide a single product wherein all of the above-described benefits can be enjoyed.

SUMMARY OF THE INVENTION

In the most general terms, the present invention comprises an assembly for centrifugally separating lymphocytes and monocytes from the heavier phases of a sample of whole blood or a pretreated cell fraction thereof and physically partitioning the separated phases. The inventive assembly consists of four basic elements:

(1) a container (customarily a blood collection tube or a centrifuge tube) having an open end and a closed end;

(2) a density gradient medium initially positioned adjacent said closed end;

(3) a partition plug initially positioned above the surface of said medium which seals said medium therebeneath; and (4) a free space initially adjacent said partition plug of sufficient volume to contain said sample and added blood anticoagulant where necessary.

A closure means for covering the open end of the container is necessary where a sterile product is demanded. Careful practice dictates utilizing a closure means during centrifugation to avoid aerosoling of the blood which may be contaminated with pathogenic materials. For conventional centrifuge tubes, a screw top cap is normally sufficient; for evacuated collection tube applications, a tight-fitting elastomeric plug is generally employed to contain the vacuum during the required storage periods.

Figure 1:
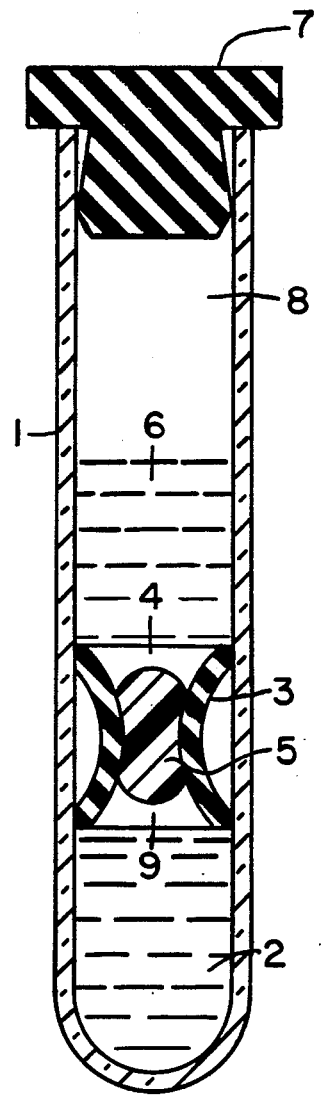
FIG. 1 comprises a schematic cross section in side elevation of one non-evacuated tube configuration of the inventive lymphocyte separation tube unit. This tube configuration is employed where a blood sample is transferred from a blood collection tube to the inventive separation tube.

FIG. 1 illustrates a preferred inventive concept while providing a specific embodiment thereof. Accordingly, to a conventional centrifuge tube 1 is added an aliquot of a density gradient medium 2 such as Ficoll-Paque ®. A stationary partition plug 3 having an aperture therethrough 4 is then inserted into tube 1 and moved to a position immediately above the surface of medium 2. Plug 3 will advantageously be fashioned from molded polypropylene having chevron-type sealing means around its periphery or molded from an inert elastomeric or plastic material having compression rings around its periphrey. A hydrophobic gel 5 of a selected density and viscosity is injected into the bore 4 of partition plug 3, thereby sealing medium 2 beneath. A free space 9 is required below the gel 5 which is of a volume approximately equivalent to that of gel 5. Thereafter, an aliquot of a suitable reagent 6, e.g., a diluent, may be added above partition plug 3. It will be appreciated that the use of a blood diluent is not mandatory but appears to promote better separation in some cases. A closure 7 is applied to the open end of tube 1 to maintain sterility therein. A free space 8 is left between the closure 7 and reagent 6, that space having a volume somewhat greater than that of the volume of the blood sample to be subject to separation. To insure that gel 5 will remain in bore 4 of partition plug 3 so as to retain density gradient medium 2 in place during shipment and storage of tube 1, and where reagent 6 is utilized, to prevent mixing of the two liquids, a non-newtonian (thixotropic) gel is preferred. Nevertheless, where table 1 is to be used relatively promptly, a newtonian gel may be used.

Figure 2:
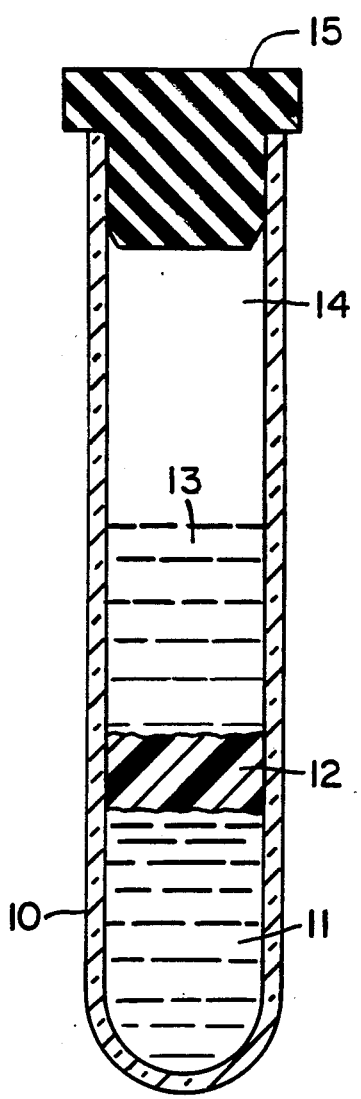
FIG. 2 comprises a schematic cross section in side elevation of one evacuated tube configuration of the inventive lymphocyte separation tube unit, which permits blood to be drawn directly from the patient into the inventive separation tube.

FIG. 2 illustrates the preferred embodiment of the present invention where the final product is an evacuated blood collection tube. In this embodiment to a conventional collection tube 10 is added an aliquot of a liquid density gradient medium 11. Partition plug 12 consists solely of a mass of a hydrophobic (thixotropic) gel which is extruded onto the surface of liquid medium 11, sealing the medium therebeneath. In like manner to the embodiment described in FIG. 1, a thixotropic gel is preferred since it insures long term sealing of medium 11 therebeneath during shipping and storage. However, a newtonian gel could self-evidently be inserted into tube 10 on site, and would perform quite satisfactorily. The gel is sufficiently tacky to adhere to the walls of tube 10. The gel has a specific gravity somewhat greater than that of liquid medium 11, thereby allowing the gel to move down tube 1 during centrifugation and so displace liquid medium 11. An aliquot of a suitable reagent 13 containing a blood anticoagulant, e.g., lithium heparin, sodium heparin, or EDTA, is added above plug 12. Free space 14 between reagent 13 and closure means 15 provides the vacuum and is of sufficient volume to permit the blood sample to be drawn directly from the patent into tube 10. Closure means 15 will conveniently be a stopper fabricated from a special butyl rubber.

As has been observed in this inventive embodiment, the partition plug moves to the bottom of the tube during centrifugation and, in so doing, displaces the liquid gradient medium. This action makes possible the separation of cell suspensions which have been previously enriched through prior separation steps. An example of that situation is the separation of "Buffy Coats". In that protocol whole blood is centrifuged or merely allowed to stand and settle out. The white cell population forms a "Buffy Coat", i.e., a buff-colored layer, on top of the mass of red cells. This layer of white cells can be removed, diluted, centrifuged, and partitioned over a gradient density medium to separate the mononuclear cells. The procedure is conducted as a means for reducing the number of separation tubes required to process an equivalent quantity of cells. The practice permits the separation of a high concentration of leukocytes utilizing a small amount of liquid medium which is very expensive. As can be seen, a mass of red cells to displace the liquid medium is not necessary in this embodiment of the inventive method, contrary to the first above-described embodiment where the partition plug remains stationary in the tube.

Isolation of lymphocytes from blood samples comprehends three general steps:

(a) a blood sample is aliquoted or drawn into a tube employing conventional techniques;

(b) the tube is rocked or otherwise agitated to mix the blood with any required reagent; and (c) the tube is centrifuged in accordance with standard techniques for separating mononuclear cells (lymphocytes and monocytes) from the heavier phases of blood utilizing a density gradient liquid procedure.

In the first inventive embodiment the gel seal is moved by the centrifugal force generated, as the tube begins to spin, into the space alloted below the partition plug. Inasmuch as the liquid medium is incompressible, the plug bore cannot be unsealed if space is not provided into which the gel can move. In FIG. 1, this space is an artifact of the small size of the bore.

The movement of the gel opens the bore and allows the red cells to pass downward into the liquid medium and, being more dense than the medium, displace the medium upward through the bore to above the partition plug. Since the volume of cells in whole blood is approximately 40%, about 8 ml of whole blood will generally displace a typical aliquot of 3 ml of density gradient medium. Where a diluent is employed, care must be exercised in practicing this inventive embodiment to have a sufficient mass of red cells to displace the liquid medium to at least its minimum operable heighth above the partition plug.

It will be appreciated that the crux of the mechanism operating in the first inventive embodiment resides in the aperture of the partition plug which confines and controls the interaction of the blood sample with the liquid medium. Hence, this inventive embodiment can be made operable without the use of a gel; the gel being a convenient means for fabricating tubes with prepackaged medium and reagent. Furthermore, this inventive embodiment envisions the use of partition inserts or plugs which fit standard sizes of centrifuge tubes, thereby enabling users the option of adjusting the amount of liquid medium desired for specific applications. This inventive embodiment also contemplates the design of a separation tube wherein the partition plug is formed as an integral part of the tube, e.g., as a raised ring projecting inwardly from the walls of the tube or a constriction in the tube. Each of the above operating modes possesses characteristics which may be of benefit for particular applications.

It will likewise be appreciated that alternative devices may be devised to close the bore of the partition plug where it is desired to ship prepackaged liquids. The preeminent requirement therefor is that the unsealing mechanism work unfailingly. For rigid and semi-rigid sealing means that work by centrifugal force, very tight control of tolerances and the elastic properties of the materials is essential. One dependable alternative comprehends the use of a rod to seal the bore; the rod extending upward to the closure of the open end of the tube and having means for grasping, such that when the closure is removed, the rod can be manually lifted out. In a variation of that alternative, the rod is capable of being removably attached to the closure such that, when the closure is taken off the tube, the rod is also removed. The rod is then detached from the closure prior to the closure being replaced upon the tube for centrifugation. Those alternatives must be so designed, however, that they do not lead to contamination of the sterile tube. In general, non-manual approaches are favored.

In the second embodiment of the invention the gel pulls away from the walls of the tube upon centrifugation and moves to the bottom of the tube. This action is sufficiently gradual that the liquid density gradient medium underlays the blood sample without appreciable mixing of the two liquids. The two principal advantages of this inventive embodiment are its ability to be utilized with "Buffy Coats", and the fact that by out-gassing both the liquid medium and the gel before assembly, evacuated blood collection tubes can be pumped down and stoppered on existing evacuation equipment. Thus, such equipment typically has the stopper positioned on top of or above the tube on pump down, allowing no room for manipulation of partition plugs or bore sealing at the pump down station.

Finally, the first embodiment of the invention can also be modified to be operable with "Buffy Coat" samples. This modification involves the use of a reagent (6 in FIG. 1) which performs the function of the red cells, viz., it displaces the liquid medium in the bottom of the tube. However, the heavy phase of this reagent must not be such as to apply additional sealing pressure to the bore which prevents upward movement of the liquid medium. One operable reagent consists of a diluent containing a quantity of heavy particles, most desirably glass microspheres, having a mass at least equal in volume to that of the liquid medium to be displaced and being inert to the medium and blood components. Because of the inherent large surface area of the glass particles, they will be in the blood which can have deleterious effects, such as activating platelets in the blood. A silicone coating applied to glass microspheres operates to preclude reaction between the blood components and the medium. The inert particles (glass microspheres) must be sufficiently small to act as a fluid and not cause a bridging action above the partition plug bore. The spherical shape of the microspheres also avoids any substantial apparent increase in the viscosity of the reagent. Because the coating of the glass particles inhibits chemical activation of blood which typically takes place where blood contacts glass, this practice is operable in all applications where a stationary partition plug is utilized along with gel or rigid plug means to seal the bore.

Yet another embodiment of the invention comprehends the use of a stationary or moveable partition plug fashioned from an integral porous foam material. A urethane foam has been particularly useful in that practice; no attachment of red cells in the foam was observed.

Where a stationary partition plug is employed, the diameter thereof will be made greater than that of the centrifuge tube such that, when inserted into the tube, it will be under sufficient compression that centrifugation will not dislodge the partition. The porosity of the foam chosen is of such fineness that, when positioned atop a density gradient medium, the foam will hold the medium in position without movement due to surface tension. Hence, no mixing of the medium and blood can be tolerated when whole or diluted blood samples are poured into the centrifuge tube. During centrifugation, however, the red cells must pass downward through the foam partition to displace the gradient medium upward through the partition. Small amounts of medium which inadvertently pass upward through the partition due to handling, shipping, barometric changes, etc., will move back through the foam as a result of capillary action after the tubes have stood upright for a period of time.

Unlike partitions prepared from solid elastomeric materials which require displacement thereof under compressive forces, i.e., they are incompressible, the foams are compressible. Spring constants of the foam materials are relatively low and tend to be more linear due to bending of the matrix rather than through compression. Consequently, wide variations in partition diameters are allowable, which circumstance makes for easy assembly. Moreover, bodies may be die cut from a sheet of foam employing very inexpensive tooling compared with such demanded in working with plastics and rubber.

The moveable partition plug can be conveniently prepackaged in a dry centrifuge tube. The diameter of the partition is made slightly smaller than that of the centrifuge tube, permitting it to float upward as the density gradient medium is poured into the tube. Two flotation mechanisms are contemplated. The first utilizes a foam having a slightly lighter density than the medium, and the second employs a foam having a density slightly greater than the medium.

Where the first mechanism is utilized, the porosity of the foam will be of such fineness that some red cells will be entrapped in the pores during centrifugation. The entrapped red cells will increase the apparent weight of the foam, thereby causing it to move downward as the red cells displace the density medium upward through the partition.

Where the second mechanism is involved, the porosity of the foam is designed such that all of the red cells will pass therethrough. The partition will float on the density medium for a period of time because of the entrapment of small air bubbles as the medium is poured into the tube. During centrifugation those air bubbles are displaced and the partition moves to the bottom of the tube. Care must be exercised to prevent an excessive quantity of air bubbles which would hazard mixing of the blood sample with the density medium as the air bubbles release.

In both mechanisms the floating partition must be of sufficient length that the addition of the blood sample will not spin or tip it. The diameter of the partition must be such as to permit free movement, but not so small as to allow mixing of the blood sample and the density medium around the perimeter thereof. Most preferably, the blood sample will be introduced from a pipette at the center of the partition and at a sufficiently slow rate that the blood does not force the partition rapidly downward into the density medium, resulting in an upsurge of medium with consequent mixing with the blood.

Finally, a stationary or a moveable partition plug can be fashioned of such length and volume of porosity as to contain the entire amount of the density gradient medium. The use of such a partition would reduce the quantity of medium needed and would better retain the medium during handling and shipping. Furthermore, there would be less tendency for "liquid hammer" to dislodge the partition during shipment. The partition would also define the foam volume that would be the interface between the density medium and blood.

DESCRIPTION OF PREFERRED EMBODIMENTS

Lymphocyte separation tube units such as are depicted in FIGS. 1 and 2 were aseptically prepared by depositing the density gradient medium, Ficoll-Paque ®, in the bottom of sterile, siliconized glass or polypropylene centrifuge tubes followed by placing a silicone-oiled, butyl rubber plug having a bore through the center thereof in contact with the surface of the medium. Polypropylene partition plugs having chevron seals on the periphery thereof were also used. A water-insoluble, thixotropic gel chemically inert to blood constituents, formulated as described in U.S. Pat. No. 4,190,535, supra, from a dimethyl polysiloxane and a methylated silica wherein the methylation renders the gel hydrophobic, and containing fillers to provide specific gravity of 1.085 thereto, was injected into the bore of the plug, thereby sealing the Ficoll-Paque ® medium therebeneath. An air bubble was left under the partition plug to allow movement of the gel upon centrifugation. To avoid mixing, the air bubble was designed to approximate the volume of gel to replace it, so that the medium would contact the blood within the bore of the plug. To simulate reagent additions, aqueous solutions were placed in contact with the gel for periods up to several months without changing the properties of the gel substantially. 10 ml glass centrifuge tubes and 50 ml plastic centrifuge tubes were assembled with partition plugs having holes of various sizes bored therethrough. The resulting assemblies were tested both with the bores open and with the bores sealed with the thixotropic gel. Whole human blood samples were pipetted into the tubes without regard for laminar flow techniques, utilizing fill times of less than 10 seconds. The tubes were immediately introduced into an unrefrigerated table top centrifuge and centrifuged at about 400 G's for about 30 minutes to achieve equilibrium.

10 ml centrifuge tubes were aseptically prepared by depositing Ficoll-Paque ® gradient medium in the bottom thereof and placing two ml of the hydrophobic gel described above in contact with and sealing the medium therebeneath. A gel of higher specific gravity was also utilized with some tubes.

Examination of the unsealed bore tube showed no mixing occurring between the blood and the liquid medium. Inspection of the tubes with bores sealed with gel found that the gel, under centrifugation, had moved down to the bottom of the tube and the medium had moved upward through the bore to assume a position underlying the blood sample. In the tubes utilizing gel alone as the partition, centrifugation caused the gel to move to the bottom of the tube, thereby displacing the liquid medium. In each tube design the Ficoll-Paque ® medium was established as a clear column of liquid above the plug. Mononuclear blood cells were seen in their classic position atop the medium. The plasma fraction of the blood and the platelets were located at the top of the centrifuge tube.

Subsequently, the plasma fraction was carefully withdrawn (pipetted off) to within a short distance above the Ficoll-Paque ® medium such that the lymphocytes and monocytes at the top surface of the medium were not disturbed. After careful removal of the layer of medium containing lymphocytes and monocytes, those cells were washed and reconstituted in an isotonic buffer solution. Thereafter, the percentage of mononuclear cells contained therein was determined in the conventional manner through hemotoxylin and eosin staining of the fixed cells. These separations were compared against the standard Ficoll-Paque ® medium separating procedure. The performance results with respect to purity, viability, and yield were essentially identical.

As can be observed from the above, the present invention offers significant improvements in ease of use and setup time without sacrificing cell purity and recovery.

We claim:

1. An assembly for centrifugally separating lymphocytes and monocytes from heavier phases of a sample of whole blood or a pretreated cell fraction thereof which comprises:
   (a) a container having an open end and a closed end;
   (b) a liquid density gradient medium initially positioned adjacent said closed end;
   (c) means for preventing mixing of the liquid density gradient medium with a blood sample prior to centrifugation of the container, the preventing means including a non-movable partition means positioned above the surface of said medium which seals said medium therebeneath prior to centrifugation and which remains stationary during centrifugations; and
   (d) a free space initially adjacent said partition means of sufficient volume to contain said sample and an added reagent where desired.

2. An assembly according to claim 1 having a closure means for sealing said open end of said container.

3. An assembly according to claim 2 wherein said closure means is suitable for vacuum sealing said open end of said container.

4. An assembly according to claim 2 wherein said closure means is pierceable buy a needle for supplying a blood sample to said container which is adapted to draw said sample.

5. An assembly according to claim 1 wherein a reagent is on top of said partition means.

6. An assembly according to claim 5 wherein said reagent consists of a diluent, a anticoagulant, or a mixture of diluent and anticoagulant.

7. An assembly according to claim 1 wherein said partition means comprises a constriction integrally formed in said container.

8. An assembly according to claim 1 wherein said partition means comprises a plug insertable into said container, said plug being stationary after insertion into said container, having a provision for air to pass through or around during insertion into said container, and means for subsequently sealing said medium therebeneath upon proper placement of said plug.

9. An assembly for centrifugally separating lymphocytes and monocytes from heavier phases of a sample of whole blood or a pretreated cell fraction thereof which comprises:
   (a) a container having an open end and a closed end;
   (b) a liquid density gradient medium initially positioned adjacent said closed end;
   (c) a non-movable partition means positioned above the surface of said medium which seals said medium therebeneath prior to centrifugation and which remains stationary during centrifugation; and
   (d) a free space initially adjacent said partition means of sufficient volume to contain said sample and an added reagent where desired;
   said partition means comprising a plug insertable into said container, said plug being stationary after insertion into said container, having a provision for air to pass through or around during insertion into said container, and means for subsequently sealing said medium therebeneath upon proper placement of said plug;
   wherein said plug has an aperture therethrough to permit said air to pass through during insertion and said aperture is subsequently sealed with a hydrophobic gel having a specific gravity greater than that of said liquid density gradient medium.

10. An assembly according to claim 9 wherein said plug is so inserted that a space is left between said plug and said liquid density gradient medium approximately equivalent to the volume of said aperture sealing gel.

11. An assembly according to claim 9, wherein said assembly contains very fine particles of high density which are inert to blood constituents and said liquid density gradient medium; said particles positioned dry or in suspension above the partition plug.

12. An assembly according to claim 11 wherein said particles are glass microspheres.

13. An assembly for centrifugally separating lymphocytes and monocytes from heavier phases of a sample of whole blood or a pretreated cell fraction thereof which comprises:
   (a) a container having an open end and a closed end;
   (b) a liquid density gradient medium initially positioned adjacent said closed end;
   (c) a non-movable partition means positioned above the surface of said medium which seals said medium therebeneath prior to centrifugation and which remains stationary during centrifugation; and
   (d) a free space initially adjacent said partition means of sufficient volume to contain said sample and an added reagent where desired;
   said partition means comprising a plug insertable into said container, said plug being stationary after insertion into said container, having an aperture therethrough to permit air to pass through during insertion into said container, and means for subsequently sealing said medium therebeneath upon proper placement of said plug;

wherein said sealing means comprises a rod-shaped element, one end of which acts to close said aperture of said plug and the other extends upwardly to closely approach or contact a closure means for sealing the open end of said container.

14. An assembly for centrifugally separating lymphocytes and monocytes from heavier phases of a sample of whole blood or a pretreated cell fraction thereof which comprises:
   (a) a container having an open end and a closed bottom end;
   (b) a liquid density gradient medium initially positioned adjacent said closed bottom end;
   (c) a partition means initially positioned above the surface of said medium which seals said medium therebeneath, said partition means being movable during centrifugation in the direction of said closed bottom end of said container; and
   (d) a free space initially adjacent said partition means of sufficient volume to contain said sample and added reagent where desired;
   wherein said partition means comprises a plug composed of an integral porous foam material having a diameter slightly smaller than said container.

15. An assembly according to claim 14 wherein said plug consists of a urethane foam.

16. An assembly for centrifugally separating lymphocytes and monocytes from heavier phases of a sample of whole blood or a pretreated cell fraction thereof which comprises:
   (a) a container having an open end and a closed end;
   (b) a liquid density gradient medium initially positioned adjacent said closed end;
   (c) a non-movable partition means positioned above the surface of said medium which seals said medium therebeneath prior to centrifugation and which remains stationary during centrifugation; and
   (d) a free space initially adjacent said partition means of sufficient volume to contain said sample and an added reagent where desired;
   wherein said partition means comprises a plug composed of an integral porous foam material having a diameter greater than that of said container such that, upon insertion into said container, sealably engages the inner walls of said container through compression.

17. An assembly according to claim 16 wherein said plug consists of a urethane foam.

* * * * *